US009238044B2

(12) United States Patent
Da Fonte Ferreira et al.

(10) Patent No.: US 9,238,044 B2
(45) Date of Patent: Jan. 19, 2016

(54) ALKALI-FREE BIOACTIVE GLASS COMPOSITION

(75) Inventors: José Maria Da Fonte Ferreira, Ilhavo (PT); Ashutosh Goel, Edison, NJ (US)

(73) Assignee: REG4LIFE REGENERATION TECHNOLOGY, S.A., Cantanhede (PT)

( * ) Notice: Subject to any disclaimer, the term of this patent is extended or adjusted under 35 U.S.C. 154(b) by 52 days.

(21) Appl. No.: 14/110,407

(22) PCT Filed: Apr. 5, 2012

(86) PCT No.: PCT/IB2012/051681
§ 371 (c)(1),
(2), (4) Date: Mar. 20, 2014

(87) PCT Pub. No.: WO2012/137158
PCT Pub. Date: Oct. 11, 2012

(65) Prior Publication Data
US 2014/0193499 A1    Jul. 10, 2014

(30) Foreign Application Priority Data
Apr. 5, 2011   (PT) .......................... 105617

(51) Int. Cl.
*A61F 2/28*       (2006.01)
*A61K 33/08*     (2006.01)
(Continued)

(52) U.S. Cl.
CPC .............. *A61K 33/08* (2013.01); *A61K 9/0024* (2013.01); *A61K 33/00* (2013.01); *A61K 33/16* (2013.01);
(Continued)

(58) Field of Classification Search
CPC ...... A61K 9/0024; A61L 27/10; A61L 27/12; A61L 27/32
See application file for complete search history.

(56) References Cited

U.S. PATENT DOCUMENTS

| 5,527,836 A | 6/1996 | Yamamuro et al. |
| 2010/0278902 A1 | 11/2010 | Jallot et al. |

FOREIGN PATENT DOCUMENTS

| WO | WO 2006/118554 A1 | 11/2006 |
| WO | WO 2009/081120 A1 | 7/2009 |

OTHER PUBLICATIONS

International Search Report, mailed Jul. 4, 2012 in connection with PCT International Application No. PCT/IB2012/051681, filed Apr. 5, 2012.

(Continued)

*Primary Examiner* — Carlos Azpuru
(74) *Attorney, Agent, or Firm* — John P. White; Cooper & Dunham LLP

(57) ABSTRACT

The present invention relates to development of bioactive glass/glass-ceramic composition that are able to promote a fast deposition layer of carbonated hydroxyapatite upon immersion in simulated body fluid (SBF) for time periods as short as one hour. Such composition might include fluorides, and a variety of oxides (or their precursor compounds), such as $Na_2O$—$Ag_2O$—$SrO$—$CaO$—$MgO$—$ZnO$—$P_2O_5$—$SiO_2$—$Bi_2O_3$—$B_2O_3$—$CaF_2$, be prepared by the melt route or by the sol-gel process, with the specific composition and the preparation route selected according to the intended functionalities, which can present controlled biodegradation rate and bactericidal activity. The powders derived from glass melts purred in cold water (frits) may completely densify by sintering at temperatures up to 800° C. without devitrification, resulting in bioglass compacts with high flexural strength (~85 MPa). The bioactive glass powders prepared by sol-gel densify at lower temperatures due to their higher specific surface area and reactivity.

18 Claims, 5 Drawing Sheets

XRD pattern of glass powder T-40 after immersion in SBF solution for 1 h.

(51) Int. Cl.
*A61K 9/00* (2006.01)
*A61L 27/32* (2006.01)
*A61L 27/10* (2006.01)
*A61L 27/30* (2006.01)
*A61K 33/00* (2006.01)
*A61K 33/16* (2006.01)
*A61K 33/42* (2006.01)
*A61L 27/58* (2006.01)

(52) U.S. Cl.
CPC ............... *A61K 33/42* (2013.01); *A61L 27/10* (2013.01); *A61L 27/306* (2013.01); *A61L 27/32* (2013.01); *A61L 27/58* (2013.01); *A61L 2400/06* (2013.01); *A61L 2430/02* (2013.01); *A61L 2430/12* (2013.01); *A61L 2430/38* (2013.01)

(56) References Cited

OTHER PUBLICATIONS

Written Opinion of the International Searching Authority, mailed Jul. 4, 2012 in connection with PCT International Application No. PCT/IB2012/051681, filed Apr. 5, 2012.

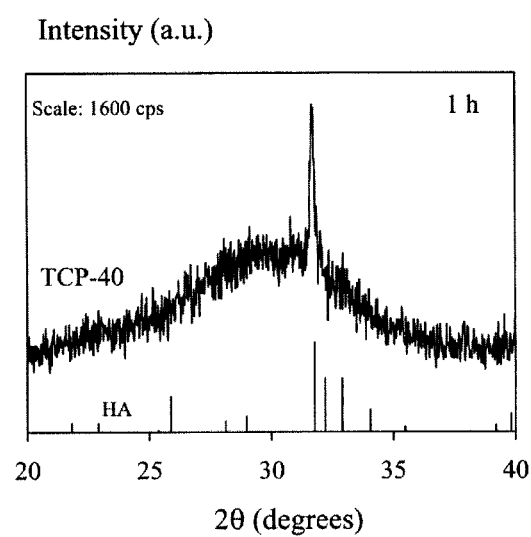
Figure 1. XRD pattern of glass powder T-40 after immersion in SBF solution for 1 h.

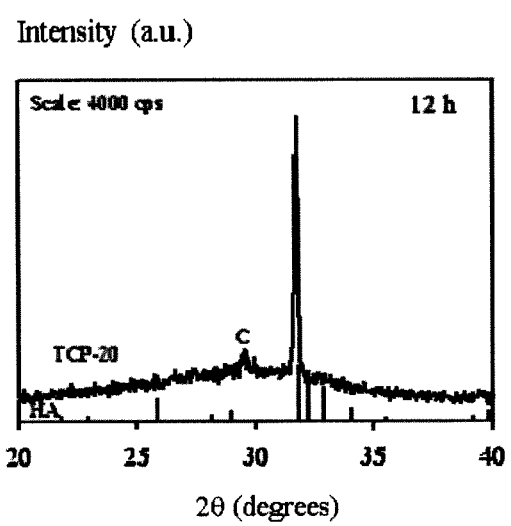
Figure 2. XRD pattern of glass powder T-20 after immersion in SBF solution for 1 h.

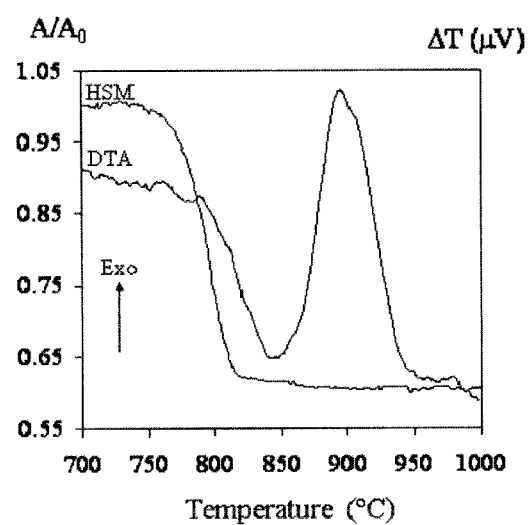
Figure 3. A comparison between hot-stage microscopy (HSM) and differential thermal analysis (DTA) for glass T-20. Heating rate: 5 K/min.

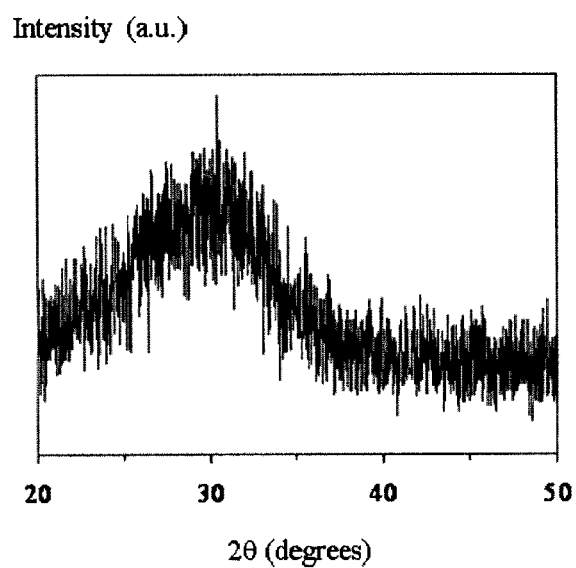
Figure 4. X-ray diffractogram of glass powder compact from composition T-20 after sintering at 800 °C for 1 h.

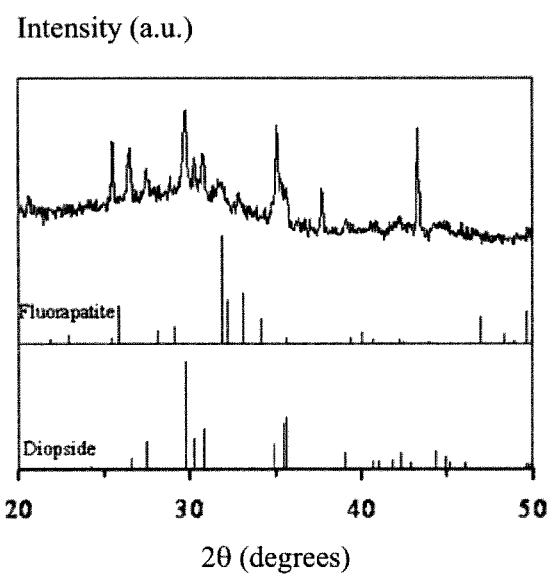
Figure 5. X-ray diffractogram of glass powder compact from composition F-20 after sintering at 850°C for 1 h.

ALKALI-FREE BIOACTIVE GLASS COMPOSITION

CROSS-REFERENCE TO RELATED APPLICATIONS

This application is a §371 national stage of PCT International Application No. PCT/IB2012/051681, filed Apr. 5, 2012, claiming priority of Portuguese Patent Application No. 105617, filed Apr. 5, 2011, the contents of each of which are hereby incorporated by reference in their entirety.

FIELD OF THE INVENTION

The present invention relates to development of set of bioactive glasses with high biomineralization rates in vitro, expressed through a fast deposition surface layer of carbonated hydroxyapatite that can be detected by X-ray diffraction, upon immersion in simulated body fluid (SBF) for time periods as short as one hour, and controlled biodegradation rates expressed by weight losses less than 2% when immersed for 5 days in a Tris HCl (pH: 7.25) solution, according to the standard ISO 10993-14 "Biological evaluation of medical devices—Part 14: Identification and quantification of degradation products from ceramics", the compositions of which can be designed in order to possess bactericidal activity, thus offering a set of essential conditions for a fast regeneration of damaged hard tissues and to avoid post-operative infections due to eventual contaminations.

BRIEF DESCRIPTION OF THE PRIOR ART

Bioactive materials are designed to induce a specific biological activity; in most cases the desired biological activity is one that will give strong bonding to bone and in some cases even with soft tissues [Rawlings, *Clin. Mater.* 14 (1993) 155-179]. Bioactive glasses and glass-ceramics are a class of bioactive materials, i.e. materials which elicit a special response on their surface when in contact with biological fluids, leading to strong bonding to living tissues. In the field of bone engineering, bioactivity is defined as the ability of the material to bond to bone tissue via the formation of a bone-like hydroxyapatite layer on its surface. Due to a number of attractive properties for use in tissue engineering and regeneration, for example: enhanced angiogenesis and up-regulation of specific genes that control the osteoblast cell cycle, there is increasing effort in the use of bioactive glasses and glass-ceramics in tissue engineering applications [Boccaccini et al., *Faraday Discuss.* 136 (2007) 27-44].

The bioactivity of silicate glasses was first observed in soda-calcia-phospho-silica glasses in 1969, resulting in the development of a bioactive glass comprising calcium salts, phosphorous, sodium salts and silicon dioxide. These glasses comprised (mol. %) $SiO_2$ (40-52%), CaO (10-50%), $Na_2O$ (10-35%), $P_2O_5$ (2-8%), $CaF_2$ (0-25%) and $B_2O_3$ (0-10%). A particular example of $SiO_2$—$P_2O_5$—CaO—$Na_2O$ bioactive glass is the 45S5 Bioglass® patented by Bench et al. in the U.S. Pat. No. 4,234,972. Although, the use of 45S5 glass in numerous clinical programs showed favourable healing capability, however, one of the main problems associated with this glass is its high dissolution rate [Sepulveda et al., *J. Biomed. Mater. Res.* 61 (2002) 301-311]. This causes fast resorption that may negatively affect the balance of natural bone remodelation and in particular the physiologically vital process of angiogenesis, thus leading to gap formation between the tissue and the implant material [Vogel et al., Biomaterials 22 (2001) 357-362].

Aiming at finding a plausible solution to the high dissolution rate of the 45S5 Bioglass®, Hench et al. have also prepared alkali-free bioglass compositions via sol-gel process in the $SiO_2$—CaO—$P_2O_5$ system as indicated in the U.S. Pat. No. 5,074,916, as well as flourine-containing 45S5 Bioglass® in which CaO was partially replaced by $CaF_2$ as described in the U.S. Pat. No. 4,775,646. However, in both cases the bioactivity of the resultant glasses was inferior in comparison to that of the 45S5 Bioglass®.

Also, owing to its poor sintering ability, there have been problems with the manufacture of highly porous scaffolds possessing good mechanical strength from 45S5 Bioglass® powder due to its poor ability to be processed in aqueous media and because of its poor sintering ability. The required mechanical properties can only be obtained through an extensive densification to strengthen the solid phase, i.e. the struts in the foam-like structure, which would otherwise be made of loosely bonded particles and thus be too fragile to handle [Clupper and Hench, *J. Non-Cryst. Solids* 318 (2003) 43-48]. Further, it has been noticed that crystallization of 45S5 Bioglass® turns this glass into an inert material [Li et al., *J. Mater. Sci. Mater. Med.* 3 (1992) 452-456].

The documents US2007162151A1 and WO2006118554A1, report on a preparation method of macroporous bioglass scaffolds with compositions that were inspired in that of "45S5 Bioglass®" of Hench et al. described in the U.S. Pat. No. 4,234,972, but enriched in CaO and $P_2O_5$, and with small added amounts of MgO and $CaF_2$: 34-50% CaO, 20-50% $SiO_2$, 0-25% $Na_2O$, 5-17% $P_2O_5$, 0-5% MgO, 0-1% $CaF_2$. Nevertheless, due to his elevated solubility in vitro, the biodegradation rates along a period of 5 days of immersion in SBF are very high, varying between 2-30%. Besides, the method of preparation of macroporous graft materials is complicated, involving coarse glass powders frits with particle sizes varying in the range of 40-300 micrometres; and pores forming organic inclusions with particle sizes varying in the range of 50-600 micrometres, the weight fraction of which can vary between 20-70%. The addition of 1-5% of polyvinyl alcohol as organic binder allows the consolidation of powder compacts by dry pressing. The gelcasting method what involves the in situ polymerization of monomers and dimers, by means of the addition of catalysts and of reaction initiators was also proposed as an alternative consolidation method. Independently of the consolidation process adopted, the powder compacts were then sintered at temperatures between 750-900° C. for 1-5 h to obtain the final product. Nevertheless, the bodies sintered at temperatures ≥800° C. were presenting the formation of wollastonite (Ca-$SiO_3$), and of tetracalcium phosphate ($Ca_4P_2O_9$), two crystalline phases that are relatively soluble in the physiologic fluid and whose dissolution makes the pH of the liquid very alkaline (pH 9-11) and damaging for the cellular activity.

The document JP3131263A proposes a series of compositions comprising the following limits for the contents of the several components: 20~60% CaO, 20~50% $SiO_2$, 0~30% $P_2O_5$, 0~20% MgO, 0-5% $CaF_2$, but enables a more fine and detailed analysis about the variation of each component and of the respective effect on the final properties of the materials.

The document JP2000271205A reports a series of compositions of bioactive glasses comprising the following limits for the contents of the several components: 30~70% CaO, 30~70% $SiO_2$, 0~40% $P_2O_5$, 0~20% MgO, 0-5% $CaF_2$, admitting also some narrower variation ranges for each component: 40~50% CaO, 30~40% $SiO_2$, 10~20% $P_2O_5$, 0.5~10% MgO, 0-2% $CaF_2$, and, namely, the following specific composition: 45% CaO, 34% $SiO_2$, 16% $P_2O_5$, 4.5% MgO, 0.5% $CaF_2$, as well as the use of these bioactive glasses as filler for bone cements based on polymetylmetacrylate (PMMA). Nevertheless, these $P_2O_5$ rich compositions present a strong tendency for the separation of liquid phases, one rich in $SiO_2$ and another rich in $P_2O_5$, as well as high biodegradation rates.

The document U.S. Pat. No. 5,527,836A also reports the use of a series of bioactive glass compositions as fillers for bone cements based on polymetylmetacrylate (PMMA). The contents of the several components in the bioactive glass compositions varied roughly within the following limits: 40-50% CaO, 30-40% $SiO_2$, 10-20% $P_2O_5$, 0-10% MgO, 0-2% $CaF_2$, although some oxides have been excluded from certain formulations, while other oxides have been included in other compositions. Namely, the following specific compositions were tested: (1) 47.7% CaO, 34% $SiO_2$, 16.2% $P_2O_5$, 4.6% MgO, 0.5% $CaF_2$; (2) 46.5% CaO, 36% $SiO_2$, 17% $P_2O_5$, 0.5% $CaF_2$; (3) 5.0% $Na_2O$, 0.5% $K_2O$, 34.0% CaO, 46% $SiO_2$, 11.5% $P_2O_5$, 3.0% MgO, 0.5% $CaF_2$, These compositions do not differ much from those proposed in the previous document, and so, they present the same liquid-liquid phase separation problems and high biodegradation rates. In an attempt to mitigate these problems presented by the glass powders, the authors used also powders that were crystallized by a thermal treatment at 1050° C. From the comparative studies, the authors concluded for the best performance of the alkaline-free glass or glass-ceramic powders, especially if combined with hydrophilic polymeric chains.

On the other hand, the apatite-wollastonite glass-ceramic (CERABONE® A-W) designed along the pseudo ternary system $3CaO.P_2O_5$—$CaO.SiO_2$—$MgO.CaO.2SiO_2$, the composition of which is described in the Japanese Patent document No. 03-131263, has been most widely and successfully used bioactive glass-ceramic for bone replacement in human medicine. The glass-ceramic composition comprises of MgO, CaO, $SiO_2$, $P_2O_5$ and $CaF_2$ wherein the weight ratio between the respective components is 4.6:44.7:34.0:16.2:0.5. The glass-ceramic exhibits particularly high bioactivity, good mechanical strength (bending strength: 178 MPa and compressive strength: 1080 MPa), and demonstrates the ability to be machined in various shapes. Further, since 1983, this glass-ceramic has been successfully used in spine and hip surgeries of patients with extensive lesions and bone defects [T. Yamamuro, A/W glass-ceramic: Clinical applications, in *An Introduction to Bioceramics*. Edited by L. L. Hench, J. Wilson World Scientific, Singapore, 1993]. However, even though, CERABONE® A-W possess the highest mechanical strength among all the bioceramics developed so far, the glass-ceramic scaffolds derived from this composition still cannot be used in load-bearing applications [Kokubo et al. *J. Mater. Sci. Mater. Med.*, 15 (2004) 99-107]. Also, there are questions raised related to the long term effect of silica, and slow degradation of this glass-ceramic, often taking some years to disappear from the body. The slow degradation of glass-ceramic scaffold may lead to reduction in its effective pore size by in vivo events such as the invasion of fibrous tissue into the pores and the nonspecific adsorption of proteins onto the material's surface.

Analogously, the U.S. Pat. No. 4,783,429 describes a biocompatible alkaline-free glass-ceramic material comprising (wt. %): 7.2-14% MgO, 25-38% CaO, 4.5-50% $SiO_2$, 8.2-25% $P_2O_5$, 0-4% $B_2O_3$, 0-3% $F_2$ and 0-6% $Al_2O_3$, in which a mixture of crystalline phases of apatite, wolastonite and diopsite is formed. Also, the U.S. Pat. No. 4,560,666 discloses a biocompatible glass-ceramic material pertaining to the system MgO—CaO—$SiO_2$—$P_2O_5$ based on the apatite and crystalline phase of alkaline-earth silicates (diopsite/akermanite/forsterite).

The sol-gel process is an alternative route to prepare bioactive glasses. In this process, the reagents (alkoxides, metal salts, etc.) are dissolved in an appropriate solvent to form a homogeneous (at the atomic scale) solution. The presence of hydrolysable groups and of water molecules gives place to the occurrence of hydrolysis and polycondensation reactions, through which small molecules give place to the formation of polymeric structures. This method involves the formation of a colloidal suspension (sol), followed by its gradual polymerization, a process that leads to the production of inorganic materials dispersed in a solvent through the growth of oxo-metal polymers, forming a porous three-dimensional structure, the viscosity of which is increasing with the time of aging, turning the whole system into a rigid gel. The gel is then thermally treated to promote the dehydration and the chemical stabilization of the powders or to densify the compacts [Hench and West, The Sol-Gel Process, 90 Chem. Rev. 33 (1990)].

The sol-gel process is an alternative an alternative route to prepare bioactive glasses at much lower temperatures, when compared with those used in the melt route process, even of more refractory alkaline-free compositions or free from other compounds with the function of fluxes. For example, the U.S. Pat. No. 5,074,916 reports on the preparation of alkaline-free bioglass formulations based only on $SiO_2$ (44-86%), CaO (4-46%), and $P_2O_5$ (3-15%) (in weight percent).

The U.S. Pat. No. 6,010,713 is a sequel of the previous patent, as well as a following up of other works from Larry L. Hench et al., and adds details about the drying step as a way of obtaining bioglass monoliths by sol-gel, according the physic-chemical principles taught by [C. Jeffrey Brinker e George W. Scherer, "Sol-Gel Science, the Physics and Chemistry of Sol-Gel Processing, Academic Press, 1990], and by [L. L. Hench, "Science of Ceramic chemical Processing", pp, 52-64, Wiley 1986].

Julian R. Jones et al. (including Larry L. Hench and other collaborators) [Julian R. Jones, Lisa M. Ehrenfried, Larry L. Hench, "Optimising bioactive glass scaffolds for bone tissue engineering", Biomaterials 27 (2006) 964-973]; [Sen Lin, Claudia Ionescu, Kevin J. Pike, Mark E. Smith and Julian R. Jones, "Nanostructure evolution and calcium distribution in sol-gel derived bioactive glass", J. Mater. Chem., 2009, 19, 1276-1282]; [Sen Lin, Claudia Ionescu, Simon Baker, Mark E. Smith, Julian R. Jones, "Characterisation of the inhomogeneity of sol-gel-derived $SiO_2$—CaO bioactive glass and a strategy for its improvement", J Sol-Gel Sci Technol (2010) 53:255-262], have been adopting simplified bioglass formulations prepared by sol-gel, and published recently a series of scientific papers dealing with the composition 70S30C (70 mol % $SiO_2$ and 30 mol % CaO). Their research efforts were aimed at finding a more appropriate solution to produce scaffolds, alternative to 45S5 Bioglass® obtained by melt route, which has serious limitations as mentioned above.

The document EP20050823528 reports on the use silver salts solutions to impregnate biocompatible glass and glass-ceramic coatings with the following molar composition: 57% $SiO_2$-34% CaO-6% $Na_2O$-3% $Al_2O_3$, applied on metallic implants in order to confer them bactericidal properties.

The main distinctive characteristics of the present invention, relatively to the state of the art, can be summarized as follows:

Bioactive glasses with an exceptionally capability of forming a surface carbonated hydroxyapatite layer when immersed in simulate body fluid, which can be detected through intense x-rays diffraction peaks, indicating a good ability for a quick bond to the bone tissues. None of the bioactive glasses previously proposed presents such levels of bioactivity in vitro.

Bioactive glasses with low solubility when compared with that of other bioglasses earlier proposed, especially those containing alkaline metals such as the 45S5 Bioglass®. This property allows the formation of a strongly adherent layer of carbonated hydroxyapatite, oppositely to what happens with the 45S5 Bioglass®, and with other inspired in it, in which the continued dissolution of the substrate ends up releasing the deposited the sets the deposited carbonated hydroxyapatite layer and, when implanted in vivo, leads to a gap formation between the implant and the bone tissue.

The low solubility also allows bioglass frits to be easily processed in aqueous environment without the risk of coagulating the suspensions (phenomenon commonly observed with the state of the art bioglass frits), the size of the particles can be sufficiently reduced to optimize the rheological properties of the suspensions for the impregnation of polymeric sponges aiming at the preparation of porous scaffolds for bone regeneration or for tissue engineering.

The low content or the absence of alkaline metals in the bioglasses from the present invention gives raise to much lower pH variations when they are in contact with the physiologic fluid in comparison to those experienced with the 45S5 Bioglass®, and with other bioglasses inspired in it. For example, from the comparison of the degradation behaviour of the bioglasses object of the present invention with the 45S5 Bioglass®, according to the standard ISO 10993-14 "Biological evaluation of medical devices—Part 14: Identification and quantification of degradation products from ceramics", in a Tris HCl (pH: 7.25) gave the following results after 5 days:

| Tested materials | Final pH | Weight loss (%) |
|---|---|---|
| Bioglasses TCP-20/TCP-40 of the present invention | Inferior to 8.50 | Inferior to 2.00 |
| 45S5 Bioglass ® | 9.68 | 3.67% |

These results show that the bioglasses from the present invention present a much lower degradation rate (less than half) of that of the 45S5 Bioglass®, and other bioglasses inspired in it.

The frit powders of the bioactive glasses disclosed in this invention can be completely densified by sintering before the occurrence of crystallization. This feature enables the obtaining implant materials with strong mechanical properties (3-point flexural strength of ≥85 MPa, the highest values ever reported for bioactive glasses).

Though the CERABONE® A-W is mechanically stronger than the bioactive glasses of the present invention, this is a glass-ceramic material with a considerable content of crystalline phases and, therefore, less bioactive.

The extremely high degree of bioactivity of the bioactive glasses of the present invention allows that it can be somewhat reduced through a partial desvitrification of around 30%, which allows to duplicate the flexural strength relative to the amorphous material, and so, to obtain a better balance between these two relevant properties.

The bioactive glasses of the present invention prepared by sol-gel can be used as coating layers of other biomaterials, including porous grafts, with the objective to stimulate the cascade of biological processes that takes place after the implantation in vivo due to his higher reactivity and better suited composition for the intended aims, including the prevention of bacteriologic contaminations, which can also accumulate other functionalities such as the storage and the controlled release of drugs in situ.

The above-mentioned distinctive characteristics show what significant progresses were done in the context of the present invention, relatively to the whole piece of information already known.

SUMMARY OF THE INVENTION

The objective of the present invention is to describe bioactive glass composition that comprises the following compounds:
  calcium oxide (CaO), between 20-60%;
  magnesium oxide (MgO), between 0-30%;
  phosphorous pentoxide ($P_2O_5$), between 0-10%;
  silica ($SiO_2$) between 29-60%;
  calcium fluoride in the form of $CaF_2$, between 0-5%,
in which all the percentages are molar percentages.

In the form of a preferential realization, the composition still comprises alkali metals in a concentration inferior to 5%.

Still in another form of a preferential realization, the composition does not contain alkali metals.

In a form of a preferential realization, the composition presents phosphorous pentoxide or silica as glass network formers.

Still in another form of a preferential realization, the bioactive glass composition comprises the following compounds:
  calcium oxide (CaO), between 25-53%;
  magnesium oxide (MgO), between 2-24%;
  phosphorous pentoxide ($P_2O_5$), between 1.7-8%;
  silica ($SiO_2$) between 29-50%;
  calcium fluoride in the form of $CaF_2$, between 0-3%,
in which all the percentages are molar percentages.

In a form of a preferential realization, the composition presents a calcium source selected from at least one of the following: calcium oxide, calcium hydroxide, calcium carbonate, calcium nitrate, calcium sulphate; calcium silicates, Still in a form of a preferential realization, the composition presents a magnesium source selected from at least one of the following: magnesium oxide, magnesium hydroxide, magnesium carbonate, magnesium nitrate, magnesium sulphate; magnesium silicates.

In a form of a preferential realization, the composition presents a phosphorous source selected from at least one of the following: phosphorous pentoxide, ammonium dihydrogenophosphate, trimethyl phosphafate, triethyl phosphate, phosphoric acid, source of phosphorous pentoxide.

Still in a form of a preferential realization, the composition presents a fluorine source selected from at least one of the following: calcium fluoride, magnesium fluoride, magnesium hydroxide, trifluoroacetic acid, hexafluorophosphate acid, ammonium hexafluorophosphate.

In a form of a preferential realization, the composition is doped with at least an oxide of one the following elements: Na, K, Li, Ru, Cs, Fr, Sr, Bi, Zn, Ag, B, Cu, Mn, Fe, Ti in molar percentages that can vary between 0-10%.

In a form of a preferential realization, the composition presents molar percentages of the doping elements that can vary between 0-5%.

In a form of a preferential realization, the composition comprises the following components:
- oxides such as $Na_2O$, $K_2O$, $SiO_2$, CaO, MgO, $P_2O_5$, $Na_2O$, $K_2O$, $Ru_2O$, $Cs_2O$, $Fr_2O$, SrO, $Bi_2O_3$, ZnO, $Ag_2O$, $B_2O_3$, $Cu_2O$, $MnO_2$, $Fe_2O_3$, $TiO_2$;
- alkoxides such as tetraethyl orthosilicate, $Si(OC_2H_5)_4$ (TEOS) or tetramethyl orthosilicate, $Si(OCH_3)_4$, (TMOS), titanium isopropoxide, $C_{12}H_{28}O_4Ti$];
- hydroxides such as NaOH, $Ca(OH)_2$, $Mg(OH)_2$, $Fe(OH)_3$;
- carbonates such as $Na_2CO_3$, $K_2CO_3$, $CaCO_3$, $MgCO_3$, $SrCO_3$;
- nitrates such as $NaNO_3$, $Ag(NO_3)$, $Mg(NO_3)_2$, $Ca(NO_3)_2$, $Ca(NO_3)_2.4H_2O$, $Ag_2(NO_3)_2$, $Fe(NO_3)_3$, $Fe(NO_3)_3.9H_2O$;
- sulphates such as $Na_2SO_4$, $K_2SO_4$, $CaSO_4$;
- phosphates or precursors of phosphor such as, ammonium dihydrogen phosphate ($NH_4H_2PO_4$), trimethyl phosphafate, $(CH_3O)_3PO$ (TMP), triethyl phosphate, $(C_2H_5O)_3PO$ (TEP), phosphoric acid, disodium hydrogen phosphate ($Na_2HPO_4$), monosodium phosphate ($NaH_2PO_4$), sodium tripolyphosphate ($Na_5O_{10}P_1$), sodium hexametaphosphate ($NaPO_3)_6$;
- fluoride or fluorine precursors such as, calcium fluoride ($CaF_2$), or magnesium fluoride ($MgF_2$), trifluoroacetic acid, $CF_3COOH$ (TFA), hexafluorophosphate acid, ($HPF_6$), ammonium hexafluorophosphate ($NH_4PF_5$);
- chlorides such as $CaCl_2$, $MgCl_2$, $FeCl_3$;
- carbonates such as $Na_2CO_3$, $K_2CO_3$, $CaCO_3$, $MgCO_3$, $SrCO_3$
- nitrates such as $NaNO_3$, $Ag(NO_3)$, $Mg(NO_3)_2$, $Ca(NO_3)_2$, $Ca(NO_3)_2.4H_2O$, $Ag_2(NO_3)_2$, $Fe(NO_3)_3$, $Fe(NO_3)_3.9H_2O$;
- borates such as sodium tetraborate ($Na_2B_4O_7.10H_2O$).

Still in a form of a preferential realization, the compositions also comprise polymeric resins.

In a form of a preferential realization, the compositions are in the powder form.

Still in a form of a preferential realization, the compositions present particle sizes inferior to 500 μm.

In a form of a preferential realization, the compositions also comprise injectable cements based on calcium phosphates or on polymethylmethacrylate.

In another form of a preferential realization, the compositions are also used in medicine.

In a form of a preferential realization, the bioactive glass compositions are used as prostheses, implants, tooth pastes, dental cements, bone fillers;

Yet in the form of a preferential realization, the bioactive glass compositions are also used in the synthesis in vitro of bone tissue;

In a form of a preferential realization, the bioactive glass compositions are used as coatings for implants, namely, orthopaedic and dental prostheses.

Still in another form of a preferential realization, the bioactive glass compositions are used in prostheses and implants made of chromium cobalt alloys, stainless steel, titanium alloys such as Ti6Al4V, polymeric materials, ceramic materials or of their mixtures.

Still another objective of the present invention is to describe the powder frits that comprise the bioactive glass compositions referred above.

Still another objective of the present invention is to describe the method for the preparation of getting powder frits that comprise the bioactive glass compositions referred above.

Still another objective of the present invention is to describe fibres, nets, meshes or discs that are made of the pharmaceutical bioactive glass compositions referred above.

Still another objective of the present invention is to describe the method of preparation of the bioactive glass compositions, which comprises the following steps:
- melting of the batches composed by mixtures of components, preferentially, oxides carbonates, nitrates, sulphates, fluorides, at temperatures in the range of 1050-1600° C. and time intervals between 1-2 h;
- pouring the melts into moulds, preferentially, metallic or graphite moulds, to obtain bulk glasses;

In the form of a preferential realization, the method still comprises an annealing step of the bioactive bulk glasses at temperatures between 400-700° C., of preference between 500-600° C.

Still in another form of a preferential realization, the method for obtaining the bioactive glass compositions comprises the following steps:
- dissolution of compounds that include: alkoxides, phosphates, fluorides, nitrates, chlorides, sulphates, oxides, acids in absolute ethanol;
- addition of water and catalysts;
- formation of a colloidal suspension;
- polymerization;
- production of inorganic colloidal materials dispersed in a solvent, through the growth of oxo-metal polymers forming a porous three-dimensional structure;
- aging and formation of the rigid gel;
- thermal treatment.

In another form of a preferential realization, the method uses water in the liquid state or in the vapour state.

Still in another form of a preferential realization, the method for obtaining the bioactive glass compositions uses a catalyst that is an acid or a base.

In another form of a preferential realization, the method for obtaining the bioactive glass compositions uses sources of $SiO_2$ that are alkoxides such as tetraethyl orthosilicate, $Si(OC_2H_5)_4$ (TEOS) and/or tetramethyl orthosilicate, $Si(OCH_3)_4$, (TMOS).

GENERAL DESCRIPTION OF THE INVENTION

The present invention provides a bioactive glasses/glass-ceramics composition, commonly designated as bioglasses/glass-ceramics, i.e., materials the elicit a special response at their surface when in contact with the biological fluids, leading to the formation of a strong connection with the living tissues through an interfacial layer of carbonated hydroxyapatite, some of them with ability to be easily sintered.

The compositions of bioactive glasses of the present invention present in general high in vitro biomineralization rates translated by the surface deposition of a carbonated hydroxyapatite layer upon immersion in simulate body fluid (SBF), which can be detected by x-rays diffraction after one hour of immersion in physiologic fluid, and controlled biodegradation rates, translated by small weight losses (<2 wt. %) when immersed during 5 days in a Tris HCl (pH: 7.25) solution according to the standard ISO 10993-14 "Biological evaluation of medical devices—Part 14: Identification and quantification of degradation products from ceramics", essential conditions to promote a fast regeneration of the hard tissues.

Further, sintering of this bioglass powder frits (glass powders derived from the glass melts by pouring them in cold water, i.e., a material usually used in the production of glazes) in the temperature interval of 800-900° C. results in well sintered and dense but amorphous glass powder compacts or glass-ceramics comprising of fine crystals of diopside ($CaMgSi_2O_6$), and/or wollastonite ($CaSiO_3$) and/or fluorapatite [$Ca_5(PO_4)_3F$] with varying degree of amorphous/crystalline ratio. The as invented bioactive glasses/glass-ceramics can be used for different applications in regenerative medicine and bone tissue engineering.

BRIEF DESCRIPTION OF THE FIGURES

For an easier understanding of the invention there are joined in annex the figures that represent results obtained with the main preferential realizations of the invention, which, nevertheless, do not intend, to limit the object of the present invention.

FIG. 1. X-rays diffraction spectra of the bioactive glass TCP-40 after immersion 0.1 g of powder from the glass in 50 ml of SBF solution during one hour. It happened that at the end of this short period of time there was a layer of carbonated hydroxyapatite (HCA) already formed onto the surface of the glass particles, confirmed by the respective peak existing in the difractogram, showing an elevated capacity up of biomineralization.

FIG. 2. X-rays diffraction spectra of the bioactive glass TCP-20 after immersion 0.1 g of powder from the glass in 50 ml of SBF solution during one hour. It happened that at the end of this short period of time there was a layer of HCA already formed onto the surface of the glass particles, confirmed by the respective peak existing in the difractogram, showing an elevated capacity up of biomineralization.

FIG. 3. Comparison between the curves of thermal differential analysis (DTA) and of hot stage microscopy (HSM) presented for the bioactive glass TCP-20. It can be observed that the temperature of maximum shrinkage occurs before the onset of crystallization, thus enabling the obtaining of completely dense glass powder compacts by a thermal treatment in the temperatures range 800-850° C. for 1 h. Heating rate: 5 K min$^{-1}$.

FIG. 4. X-rays diffraction spectra of a bioactive glass powder compact of TCP-20 sintered at 800° C. for one hour, confirming the amorphous nature of the well densified material, as one can deduce from its high mechanical flexural strength (85 MPa).

FIG. 5. X-rays diffraction spectra of a bioactive glass powder compact of FA-20 sintered at 850° C. for one hour, giving raise to the formation of a glass-ceramic with about 30 wt. % of crystalline phases. The diopside is the main crystalline phase, being the fluorapatite present as secondary crystalline phase.

DETAILED DESCRIPTION OF THE INVENTION

The present invention provides a bioactive glass composition series with enhanced bioactivity, some of them with good sintering ability. The bioactive glass of the present invention thereby provides an increased rate of apatite deposition and controlled biodegradation, leading to rapid repair and reconstruction of diseased and damaged tissues.

Further, bioactive glass powder compacts prepared from the glass flits obtained by pouring the glass melts in cold water can be sintered in temperature interval of 800-900° C. resulting in full dense but amorphous materials or in glass-ceramics comprising of fine crystals of diopside ($CaMgSi_2O_6$), and/or wollastonite ($CaSiO_3$) and/or fluorapatite [$Ca_5(PO_4)_3F$] with varying degree of amorphous/crystalline ratio. The as invented glass-ceramics can be used for different applications in bone tissue engineering.

The bioactive glass compositions disclosed in this invention may be synthesized by melt-quenching technique that involves melting of respective batches comprised of oxides, carbonates, nitrates, sulphates, fluorides, etc., in crucibles of Pt or other suitable materials, in the temperature range of 1500-1600° C. for time duration varying between 1-2 h, followed by pouring the melts in moulds of metal or graphite, or other appropriate materials, in order to obtain bulk glasses, or by pouring in cold water to obtain glass frits for the processing of materials via powder compaction and sintering.

Alternatively, the bioactive glass object of the present invention can be prepared by sol-gel from solutions of alkoxides, phosphates, fluorides, nitrates, chlorides, sulphates, oxides, acids etc. . . . The reagents are normally dissolved in absolute ethanol and the hydrolysis reactions are induced by controlled additions of liquid water or in the form of steam and of catalysts (acid or basic).

This method involves the formation of a colloidal suspension (sol), pursued by its gradual polymerization, thus leading to the production of inorganic materials dispersed in a solvent, through the growth of oxo-metal polymers forming a porous three-dimensional structure, which viscosity is increasing with the time of aging, turning the sol into a rigid gel. The gel is then thermally treated to promote the dehydration and the chemical stabilization of the powders or to sinter the compact.

The description about the sources of glass components, their roles in tailoring the bioactive behaviour of glasses and the reasons about limiting each component of glass/glass-ceramic of present invention to above described ranges are presented below.

Silica ($SiO_2$) and phosphorus pentoxide are two main glass network formers and is the most essential component for the formation of a bioactive glass, although their respective structures exhibit limited miscibility. Therefore, one of these oxides has to play the main role in a given composition. Otherwise, there will be the occurrence of liquid-liquid phase separation during melting and cooling; leading to structural heterogeneities and the as obtained glass is prone to easily degrade upon immersion in SBF or even in pure water.

Silica ($SiO_2$) is the typical glass network former and is the most essential component for the formation of a bioactive glass. The molar percentage of $SiO_2$ in the glass prepared by melt route affects its glass forming ability, molecular structure, along with its sintering and crystallization ability.

The molecular structure of glass plays a crucial role in deciding their bioactivity. The high level of bioactivity in glasses is known to arise from a structure dominated by chains of $Q^2$ metasilicates, which are occasionally cross-linked through $Q^3$ units, whereas $Q^1$ species terminate the chains, where $Q^n$ species distribution furnishes a measure of the connectivity of the glass network and the index n refers to the number of bridging oxygens (BOs) surrounding a network former ions. Similarly, the enhanced dissolution of silica in highly bioactive compositions has also been found to be closely related to the significant fraction of $Q^1(Si)$ chain terminators while moderate bioactivity can be achieved when $Q^3(Si)$ structures predominate [Tilocca, Proc. R. Soc. A 465 (2009) 1003-1027].

Also, when in contact with SBF, the loss of silica species from glass indirectly enhances the bioactive behaviour through the surface Si-OH groups generated in the Si—O—Si hydrolysis process which in turn decrease the interface energy between apatite and glass. The soluble silica species also play a direct role as nucleation centres for precipitation of calcium phosphate; new applications of bioactive glasses as scaffolds for in vitro tissue engineering require the direct action of released silica and calcium in activating genes which induce osteoblast proliferation [Tilocca et al. *Faraday Discuss.* 136 (2007) 45-55].

As stated above, when the glasses of the present invention are prepared by the melt-quenching technique, therefore, the molar percentage of $SiO_2$ in glasses is preferably 29-60%. If the molar percentage of $SiO_2$ is below 29%, the glass is prone to extensive crystallization immediately after casting of melt. Therefore, the amount of $SiO_2$ is 29% at minimum, or preferably 29.5% or more. Similarly, the use of $SiO_2$ more than 60% decreases the glass forming ability and leads to extensive crystallization of glass melt. Therefore. $SiO_2$ content is 60% maximum, or preferably 50%. In case of the glasses prepared by sol-gel, the content of silica can reach values up to around 90%. In this case, the sources of $SiO_2$ can be alkoxides, such as tetraethyl orthosilicate, $Si(OC_2H_5)_4$ (TEOS), tetramethyl orthosilicate, $Si(OCH_3)_4$, (TMOS). On the other hand, in the glasses in which the $P_2O_5$ is the predominant glass forming oxide, the molar percentage of $SiO_2$ can be of around 10% or even inferior.

The bioactive glasses of the present invention comprise a source of calcium including but not limited to calcium oxide (CaO), calcium carbonate ($CaCO_3$), calcium nitrate ($Ca(NO_3)_2$), calcium sulphate ($CaSO_4$), calcium silicates or a source of calcium oxide. For the purpose of this invention, a source of calcium oxide includes any compound that decomposes to form calcium oxide. Release of $Ca^{2+}$ ions from the surface of a bioactive glass aids the formation of the calcium phosphate-rich layer. Therefore, for the purpose of the first aspect of the invention, the molar percentage of CaO in glasses is 20-60%. Preferably, the molar percentage of CaO in bioactive glass is 20-55%. More preferably, the molar percentage of CaO in bioactive glass is 25-53%.

The bioactive glass of the present invention preferably comprises a source of magnesium including but not limited to magnesium oxide (MgO), magnesium carbonate ($MgCO_3$), magnesium nitrate ($Mg(NO_3)_2$), magnesium sulphate ($CaSO_4$), magnesium silicates or a source of magnesium oxide. For the purpose of this invention, a source of magnesium oxide includes any compound that decomposes to form magnesium oxide. Recent data indicates that magnesium can act as an intermediate oxide and partially as a network modifier [Watts et al. *J. Non-Cryst. Solids* 356 (2010) 517-524]. Magnesium ions decrease the size of the HCA crystals formed and decrease the thermal expansion coefficient of the glass. This is advantageous when the bioactive glass is intended for use as a coating, for example, as a coating on metal prosthesis, including but not limited to those comprising metal alloys such as Ti6Al4V. In higher concentrations, magnesium ions tends to associate preferentially with phosphorus at glass surface, which consequently leads to the decrease in concentration of apatite like-calcium phosphate domains on the surface glass that are supposed to act as nucleation centres for apatite formation and therefore, suppress the crystallization of apatite and favour the formation of amorphous calcium phosphate [Pérez-Pariente et al. *Chem. Mater.* 12 (2000) 750-755; Jallot, *Appl. Surf. Sci.* 211 (2003) 89-95].

Preferably, the molar percentage of magnesium (MgO) is in the range of 0-30%. Preferably, the molar percentage of MgO in bioactive glasses is comprised in the range of 0-25%. More preferably, the molar percentage of MgO in bioactive glasses is restricted to the range of 2-24%.

The bioactive glass of the present invention preferably contains a source of $P_2O_5$ including but not limited to phosphorous pentoxide ($P_2O_5$), ammonium dihydrogen phosphate ($NH_4H_2PO_4$), trimethyl phosphafate, $(CH_3O)_3PO$ (TMP), triethyl phosphate, $(C_2H_5O)_3PO$ (TEP), phosphoric acid, or another source of phosphorous pentoxide. For the purpose of this invention, a source of phosphorous pentoxide includes any compound that decomposes to form phosphorous pentoxide. The structural arrangement of phosphate groups in the bioactive glass plays a crucial role in deciding their rate of bioactivity. In order to have enhanced bioactivity, phosphate in the glass structure should preferably exist in orthophosphate ($Q^0$) environment. The release of phosphate ions from the surface of the bioactive glass aids in the formation of HCA. Whilst HCA can form without the provision of phosphate ions by the bioactive glass, as body fluid contains phosphate ions [De Aza et al. *J. Biomed. Mater. Res. B: Appl. Biomater.* 73B (2005) 54-60], the provision of phosphate ions by the bioactive glass increases the rate of formation of HCA and bone bonding ability [Tilocca, *Proc. R. Soc. A* 465 (2009) 1003-1027]. In addition, $P_2O_5$ has a beneficial effect on the viscosity-temperature dependence of the glass, increasing the working temperature range, which is advantageous for the manufacture and formation of glass. Also, $P_2O_5$ addition decreases the coefficient of thermal expansion of glass due to re-polymerization of silicate network [Kansal et al. *Acta Biomater.* (2010) doi:10.016/j.actbio.2010.05.019]. This is advantageous when the bioactive glass is intended for use as a coating, for example as a coating on metal prosthesis, including but not limited to those comprising metal alloys such as Ti6Al4V. In small amounts, $P_2O_5$ acts as sintering additive, thus enhancing the sintering ability of glass powders. This is advantageous when 3D porous scaffolds are intended to be fabricated by sintering and crystallization of bioactive glass powders. In higher concentrations, phosphate in glass tends to deviate from its orthophosphate type structure, thus reducing the bioactivity of the glass.

The molar percentage of $P_2O_5$ in the present invention therefore in limited to 0-10% in glasses in which silica is the main glass forming oxide. Preferably, the molar percentage of $P_2O_5$ in these bioactive glasses is 0-8%. More preferably, the molar percentage of $P_2O_5$ in these bioactive glasses is in the range of 1.7-8%. On the other hand, in glasses in which $P_2O_5$ is the main glass forming oxide, its percentage in that glasses is comprised in the range of 30-50%. Preferably, the molar percentage of $P_2O_5$ in these bioactive glasses is in the range of 33-40%.

The bioactive glass of the present invention preferably comprises fluorine. Preferably fluorine is provided in the form of one or more fluorides such as calcium fluoride ($CaF_2$), or magnesium fluoride ($MgF_2$), trifluoroacetic acid, $CF_3COOH$ (TFA), hexafluorophosphate acid, ($HPF_6$), ammonium hexafluorophosphate ($NH_4PF_6$), etc. . . . Fluoride stimulates osteoblasts, controls dissolution of glass and increases bone density due to which fluoride releasing implants are of interest for patients suffering from osteoporosis [Brauer et al. *Acta Biomater.* 6 (2010) 3275-3282]. Fluoride also promotes the formation of more mixed-type apatite structures with a greater similarity to natural biological forms by substituting readily for hydroxyl ions in the apatite lattice. The mixed apatite is more thermodynamically stable and therefore less soluble and less resorbable. Also, fluoride is a well-documented anti-carcinogenic agent. Fluoride released from dental restorative materials prevents demineralization and promotes the remineralisation of dental hard tissues [Wiegand et al. *Dental Mater.* 23 (2007) 343-362].

Preferably the source of fluorine (preferably $CaF_2$, in the case of glasses prepared by the melt-quenching technique, or by hexafluorophosphate ($HPF_6$), in the case of glasses prepared by sol-gel) is provided in a molar percentage of 0-5 mol. %. Preferably, the molar percentage of $CaF_2$ in bioactive glass is 0-3 mol. %. More preferably, the molar percentage of $CaF_2$ in bioactive glass is 0.5-2 mol. %. It should be noted that in vitro, only small amounts of fluoride (approximately 0.03-0.08 ppm) in remineralizing solutions are necessary to shift the equilibrium from demineralization to remineralization [Wiegand et al. Dental Mater. 23 (2007) 343-362]. An increase in fluoride concentration in glass might degrade the bioactivity of the glass as fluoride is known to inhibit the dissolution of glasses [Lusvardi et al. Acta Biomater. 5 (2009) 3548-3562].

Most bioactive glass compositions, currently available, contain sodium oxide ($Na_2O$) and may also contain potassium oxide ($K_2O$). The incorporation of these compounds in bioactive glass although is advantageous for the production of bioactive glass, as they reduce the melting temperature of the glass but the presence of alkali metals, sodium and potassium, in bioactive glass can reduce the usefulness of the glass in vivo. In particular, the bioactive glasses having high alkali metal content are susceptible to water uptake by osmosis resulting in swelling and cracking of polymer matrix embedding them in composites and might, in case of degradable polymer composites, exhibit increased levels of degradation. Such, bioactive glasses may also be unsuitable for use as coatings for metal prosthetics due to increased coefficient of thermal expansion owing to the presence of alkali metals. Furthermore, high levels of alkali metals degrade the sintering ability of bioactive glasses by increasing the crystallization tendency of glass, thus, rendering them unfit for use as bioactive porous scaffolds or porous coatings. Therefore, preferably, the total molar percentage of alkali oxides in the bioactive glass compositions of the present invention should be inferior to 10%, preferentially inferior to 5%, or even preferentially alkali-free.

The incorporation of boron oxide ($B_2O_3$) in the bioactive glass formulations of the present invention is based on recent evidences about its beneficial effect on the remodelling and healing of bone [A. Gorustovich, J. M. Porto López, M. B. Guglielmotti, R. L. Cabrini, Biomed. Mater. 2006, 1, 100]; [A. Gorustovich, T. Steimetz, F. H. Nielsen; M. B. Guglielmotti, Arch. Oral Biol. 2008, 53, 677], and a bactericidal action against the Staphylococcus aureus [E. Munukka, O. Leppäranta, M. Korkeamäki, M. Vaahtio, T. Peltola, D. Zhang, L. Hupa, H. Ylänen, J. I. Salonen, M. K. Viljanen, F. Eerola, J. Mater. Sci. Mater. Med. 2008, 19, 27]. Besides, boron oxide acts as fluxing agent lowering the viscosity of the melts and its dependence of the temperature, and extends the scale of working temperatures, facilitating the formation and the production of the glass. Nevertheless, the molar percentage of boron oxide must not be superior to 8%, it must preferentially be inferior to 5%.

The incorporation of doping oxides, such as the strontium oxide, the bismuth oxide and the zinc oxide, is justified by their beneficial effects derived from the gradual lixiviation of the respective ions in the physiologic fluid, stimulating the enzymatic and cellular activity. The molar percentage of each one of these oxides can vary between 0-10%, mainly between 2 and 6%.

Aluminium is a neurotoxin and inhibitor of the in vivo bone mineralization even at very low levels, for example <1 ppm. Therefore, preferably, the bioactive glass of the present invention is aluminium-free as described in the USA patent document No. 2009/0208428 A1.

Depending on its intended use, the bioactive glass of the present invention may be in particulate form, or in monolith bulk forms such as disks or other regular or non-regular geometrical shapes. In particular, the glass can be provided in any required shape or form, for example as a pellet, sheet, disk, fibre, etc. In particulate form, the preferred particle size depends upon the application of bioactive glass in question; however, preferred ranges of particle sizes are less than 500 µm.

In some embodiments, the composition of a bioactive glass of the present invention is tailored to provide the glass with a large processing window, resulting from a large gap between the glass transition temperature ($T_g$) and the onset of crystallization ($T_c$). Such glasses are particularly suitable for drawing into fibres and for sintering powder compacts because the large processing window allows the drawing of the glass into fibres to proceed without the occurrence of crystallization. The molten bioactive glass poured in cooled moulds of materials with good thermal conductivity (ex.: brass, graphite, etc.) maintain their glass structure, making them so suitable for drawing of fibres in air, a process that involves a faster and more abrupt cooling due to the reduced diameter of the fibres (of the order of tens of micrometres) than in the case of which in case of poured the melts in cooled moulds, so guaranteeing the maintenance of the glass phase in the fibres, which in turn can be woven according to varied architectures.

Another relevant characteristic is that the present invention provides glass powder compacts which are either completely amorphous or comprise of fine crystals of diopside ($CaMgSi_2O_6$) and/or wollastonite ($CaSiO_3$) and may also contain crystals of fluorapatite [$Ca_5(PO_4)_3F$], which can be consolidated by several shaping techniques followed by sintering. The consolidation techniques can include the dry pressing, and colloidal processing from aqueous or non-aqueous suspensions such as slip casting, tape casting, injection moulding, and by direct consolidation techniques (that do not involve the removal of the dispersing liquid, such as: the in situ polymerization or gel casting, starch consolidation, direct coagulation casting, freeze casting, temperature induced forming, temperature induced gelation, etc. . . . The sintered glass powder compacts disclosed in this invention are synthesized from glass compositions disclosed above, which possess good sintering ability. Further, the sintered bodies possess high mechanical strength and controlled biodegradability.

The glass-ceramics disclosed in this invention are synthesized by sintering and crystallization of glass powders with their mean particle size in the range of 1-20 µm, followed by sintering. The glass powders are sintered in temperature interval of 800-900° C. for time duration varying between 30 min-60 min in order to obtain glass-ceramics with different amorphous/crystalline content ratio which in turn allows obtaining glass-ceramics with varying degree of bioactivity and mechanical strength.

The good sintering behaviour in glasses is achieved if molar percentage of $SiO_2$ in glasses is preferably 34-50%. If the molar percentage of $SiO_2$ is below 34%, the crystallization precedes sintering, thus resulting in a poorly sintered and fragile glass-ceramic. Therefore, the amount of $SiO_2$ is 34% at minimum, or preferably 34.1% or more. Similarly, the use of $SiO_2$ more than 50% decreases the sintering ability and leads to extensive crystallization of glass melt, thus converting the glass-ceramic to be bio-inert. Therefore, $SiO_2$ content is 50% maximum, or preferably 46.4%.

A third relevant feature of the invention relates to potential uses of the bioactive glass of the invention in regenerative medicine, preferably in applications related to the prevention and/or treatment of damage to tissue.

For the purpose of this invention, the tissue can be bone tissue, cartilage, soft tissues including connective tissues and dental tissues including calcified dental tissues such as enamel and dentin.

The damaged tissues of those that are intended to be treated with the bioactive glass of the invention can be animal tissues, more preferably mammalian or human tissues. The bioactive glass are preferably provided for use in humans or animals such as dogs, cats, horses, sheep, cows or pigs, etc. . . .

The bioactive glasses of the present invention are aimed to prevent or treat damaged tissues. In particular, the damage to tissues, or defect, may be caused by or may be a result of accidents, or diseases such as osteoarthritis, periodontal, the removal of tumours such as osteosarcoma, etc. . . .

The provision of bioactive glasses of the present invention allows the repair and reconstruction of damaged tissues. In particular, it was observed that the immersion of bioactive glass in body fluid results in the formation of HCA layer at required site of action and the activation of in vivo mechanism of tissue regeneration. It is proposed that application of the bioactive glass to damaged tissues stimulates the deposition of the HCA on the bioactive glass and the surrounding tissues. The bioactive glasses therefore cause repair of damaged tissues by initiating/stimulating deposition of HCA thereby initiating and/or stimulating deposition of HCA thereby initiating and/or stimulating regeneration of the damaged tissue.

The bioactive glasses of the present invention provide the particular feature of being suitable for uses in percutaneous vertebroplasty or kyphnoplasty, two minimally invasive surgical procedures for increasing spinal stability and relieving back pain caused by fractured vertebrae. The bioactive glass may be incorporated into polymeric cement, generally polymethylmetacrilate, or in calcium phosphate based cements and injected into the vertebral space to prevent osteoporotic fractures and vertebral collapse associated with osteoporosis and resulting in curvature of the spine or to restore height to the vertebrae.

The bioactive glasses disclosed in this invention can also be used to treat damaged tissues in the dental cavity, preferentially, in the treatment of periodontal diseases. In particular, the bioactive glasses are used to promote HCA deposition and bone formation at sites where periodontal diseases have resulted in the destruction of bone that supports the tooth. Further, the bioactive glasses may be used for treatment of dental caries. The particular application of bioactive glasses for treatment of caries will result in elevated salivary fluoride levels which are of most benefit in preventing/treating caries. Also, the bioactive glass of third aspect can be used as a cariostatic agent and inhibit tooth demineralization. The fluoride leached from bioactive glass of third aspect may precipitate on the tooth surface as calcium fluoride-like layer, which serves as a reservoir for fluorides when the pH drops. This calcium fluoride-like material, so-called KOH-soluble fluoride, facilitates the re-precipitation of minerals by forming fluoroapatite or fluorohydroxyapatite, thereby preventing further loss of mineral ions. Such bioactive glass, for example, can be incorporated into toothpastes, chewing gums, dentifrices or mouth wash.

The administration of bioactive glasses disclosed in this invention results in an increase in pH at the site of action of the bioactive glass due to physicochemical reactions on the surface of the bioactive glass. Bacteria found on the surface of the human skin which thrive under acid conditions are inhibited by the alkaline conditions produced by the bioactive glass. Therefore, bioactive glass of third aspect is provided for the prevention and/or treatment of a bacterial infection associated with damage to a tissue.

The fourth relevant feature of the present invention is to provide implant coating materials comprising the bioactive glasses described above.

The coatings can be used to coat metallic implants for insertion into the body, combining the excellent mechanical strength of implant materials like metals and alloys such as Ti6Al4V and chrome cobalt alloys, plastic and ceramic, and the biocompatibility of the bioactive glass. The bioactive glass coatings can be applied to the metallic implant surfaces by methods including but not limited to enamelling or glazing, flame spraying, plasma spraying, rapid immersion in molten glass, dipping into slurry of glass particles in a solvent with a polymer binder, or electrophoretic deposition.

The bioactive coating allows the formation of a hydroxycarbonated apatite layer on the surface of the prosthesis, which can support bone ingrowths and Osseo integration. This allows the formation of an interfacial bone between the surface of the implant and the adjoining tissue. The prosthesis is preferably provided to replace a bone or joint such as comprise hip, jaw, shoulder, elbow or knee prostheses. The prosthesis referred to in the present invention can be used in replacement surgeries of the respective damaged articulations for restoring the lost functionalities. The bioactive glass coatings of the present invention can also be used to coat orthopaedic devices such as the femoral component of total hip arthroplasties or bone screws or nails in fracture fixation devices.

A particular feature of this invention is to provide bioactive porous scaffolds comprising the bioactive glasses described above. Preferably, the bioactive porous scaffolds are used for tissue engineering. The porous scaffolds can be used for in vitro synthesis of bone tissue when exposed to a tissue culture medium and inoculated with cells. The bioactive properties of such scaffolds allow the formation of a strong interface between the bone tissue and the scaffold, and the induction of osteoblast proliferation. Amongst other uses, the bone tissue formed on the bioactive porous scaffolds can be inserted into areas that exhibit increased risk of fracture, and decreased or even extinct potential for bone tissue formation. In particular, the bone tissue can be used to replace damaged or diseased bone.

The invention may be put into practice in various ways. A number of specific embodiments are described as illustrative examples of some of the most relevant features of the invention with reference to the accompanying drawings, which make integrant part of the invention, but the scope of the invention is not limited to the presented examples.

Applications of the Invention in the Technological and Other Areas

The tests carried out to value the properties of the developed materials and their potential uses are described below. Throughout the examples set out below, molar percentage values were calculated in accordance with standard practice in the art.

Thermal Behaviour of Glasses

The coefficient of thermal expansion (CTE) of glasses was obtained from dilatometry measurements which were carded out on prismatic glass samples with a cross-section of 4×5 mm (Bahr Thermo Analyze DIL 801 L, Hüllhorst, Germany; heating rate 5 K $min^{-1}$).

The sintering behaviour of the glass powders was investigated by hot-stage microscopy (HSM) using particle sizes in the range of 5-20 µm. The image analyser takes into account the thermal expansion of the alumina substrate while measuring the height of the sample during firing, with the base as a reference. The HSM software calculates the percentage of decrease in height, width and area of the sample images. The measurements were conducted in air at a heating rate of 5 K min$^{-1}$. The cylindrical samples with height and diameter of ~3 mm were prepared by cold-pressing the glass powders. The cylindrical samples were placed on a 10×15×1 mm$^3$ alumina (>99.5 wt. % Al$_2$O$_3$) support. The temperature was measured with a Pt/Rh (6/30) thermocouple contacted under the alumina support. The measurements were conducted in air at a heating rate of 5 K min$^{-1}$. The cylindrical samples with height and diameter of ~3 mm were prepared by cold-pressing the glass powders. The cylindrical samples were placed on a 10×15×1 mm$^3$ alumina (>99.5 wt. % Al$_2$O$_3$) support. The temperature was measured with a Pt/Rh (6/30) thermocouple contacted under the alumina support.

The crystallization behaviour of glasses was studied using differential thermal analysis (DTA-TG; Setaram Labsys, Setaram Instrumentation, Caluire, France) of glass powders carried out in air from room temperature to 1000° C. with heating rates ($\beta$) of 5K min$^{-1}$, using particle sizes in the range of 5-20 μm.

In Vitro Bioactivity Analysis in SBF

The in vitro bioactivity of the glasses, reflected in their capability of inducing HCA-formation onto their surfaces, was investigated by immersion of glass powders in SBF solution at 37° C. SBF had ionic concentrations (Na$^+$ 142.0, K$^+$ 5.0, Ca$^{2+}$ 2.5, Mg$^{2+}$ 1.5, Cl$^-$ 125.0, HPO$_4^-$ 1.0, HCO$_3^{2-}$ 27.0, SO$_4^{2-}$ 0.5 mmol l$^{-1}$) nearly equivalent to human plasma, as discussed by Tas [*Biomaterials* 21 (2000) 1429-1438].

In all embodiments, the glass powders with mean particle size varying between 5-20 μm and weighing 0.1 g were immersed in 50 ml of SBF at pH 7.25 and placed at 37° C. for time periods of 1 h, 3 h, 6 h, 12 h, 24 h, 72 h, 168 h and 336 h unless otherwise specified. The SBF solution was replaced after every 48 h.

In some embodiments, the glass powders with mean particle size varying between 5-20 μm and weighing 0.25 g were immersed in 50 ml of SBF at pH 7.25 and placed in an orbital shaker at 2 Hz and 37 ° C. for time periods of 1 h, 3 h, 6 h, 12 h, 24 h, 72 h, 168 h, 336 h and 672 h unless otherwise specified. The filtered solution was then analysed by inductively coupled plasma (ICP)-atomic emission spectroscopy (AES) to determine the concentrations of Si, Ca, Mg and P.

In some embodiments, sintered glass powder compacts with diameter varying between 8-9 mm and weighing 0.5 g were immersed in 50 ml of SBF at pH 7.25 and placed at 37° C. for time periods of 1 h, 3 h, 6 h, 12 h, 24 h, 72 h, 168 h and 336 h unless otherwise specified. The SBF solution was replaced after every 48 h.

In some embodiments, sintered glass powder compacts with diameter varying between 8-9 mm and weighing 0.5 g were immersed in 50 ml of SBF at pH 7.25 and placed in an orbital shaker at 2 Hz and 37° C. for time periods of 1 h, 3 h, 6 h, 12 h, 24 h, 72 h, 168 h, 336 h and 672 h unless otherwise specified. The filtered solution was then analysed by inductively coupled plasma (ICP)-atomic emission spectroscopy (AES) to determine the concentrations of Si, Ca, Mg and P.

In addition to the characterisation tests referred above, the formation of an FICA layer at the surface of the glass was monitored by x-ray powder diffraction and Fourier transform infra-red spectroscopy (FTIR).

For easier understanding of the invention, in the following examples describe some aspects examples that represent preferential invent realizations, which, nevertheless, do not intend to limit the scope of the present invention.

EXAMPLE 1

Exceptional Biomineralization Capability

A glass labelled as 'T-40' with composition 45.08 CaO-14.72 MgO-10.12 P$_2$O$_5$-29.45 SiO$_2$-0.63 CaF$_2$ (mol. %) was prepared through melt-quenching technique. The high purity powders of SiO$_2$, CaCO$_3$, MgCO$_3$, NH$_4$H$_2$PO$_4$ and CaF$_2$ were used. Homogeneous mixtures of batches obtained by ball milling were preheated at 900° C. for 1 h for calcination and then melted in Pt crucible at 1590° C. for 1 h. The glass flits were obtained by quenching of glass melt in cold water. The frits were dried and then milled in a high-speed agate mill, resulting in fine glass powders with mean particle sizes of ~5-20 μm. The amorphous nature of glasses was confirmed by XRD analysis.

As described above, 0.1 g of glass powder was immersed in 50 ml SBF solution for time period varying between 1 h-14 days. The glass powder exhibited the formation of HCA layer on its surface after 1 h of immersion in SBF solution, thus indicating a very high rate of bioactivity (FIG. 1). These results demonstrate that this glass may be used in various orthopaedic as well as dental applications as detailed in the description of the invention.

EXAMPLE 2

High Biomineralization Capability

The glasses with compositions as presented in Table 1 were prepared through melt-quenching technique and crushed to powder form with mean particle sizes between 5-20 μm, in accordance with the details explained in Example 1. The amorphous nature of glasses was confirmed by XRD analysis.

TABLE 1

| Vidro | Bioglass compositions (mol. %) | | | | |
|---|---|---|---|---|---|
| | MgO | CaO | P$_2$O$_5$ | SiO$_2$ | CaF$_2$ |
| FA-30 | 19.25 | 35.18 | 5.31 | 38.49 | 1.77 |
| FA-40 | 17.07 | 39.04 | 7.33 | 34.12 | 2.44 |
| W-80 | — | 53.03 | 3.64 | 42.12 | 1.21 |
| TCP-20 | 19.24 | 36.07 | 5.61 | 38.49 | 0.59 |

As described above, 0.1 g of respective glass powders was immersed in 50 ml SBF solution for time period varying between 1 h-14 days. The glass powder exhibited the formation of HCA layer on its surface after 12 h of immersion in SBF solution, thus indicating a high rate of bioactivity (FIG. 2). These results demonstrate that the bioglass compositions reported in Table 1 may be used in various orthopaedic as well as dental applications as detailed in the description of the invention.

EXAMPLE 3

Good Sintering Ability

The glasses with composition as presented in Table 2 were prepared through melt-quenching technique and crushed to powder form with mean particle sizes between 5-20 μm in accordance with the details explained in Examples 1 & 2. The amorphous nature of glasses was confirmed by XRD analysis.

TABLE 2

Bioglass compositions (mol. %)

| Glass | MgO | CaO | $P_2O_5$ | $SiO_2$ | $CaF_2$ |
|---|---|---|---|---|---|
| F-10 | 23.20 | 28.18 | 1.66 | 46.41 | 0.55 |
| F-20 | 21.29 | 31.57 | 3.43 | 42.57 | 1.14 |
| T-10 | 21.29 | 32.00 | 3.57 | 42.57 | 0.57 |
| T-20 | 19.24 | 36.07 | 5.61 | 38.49 | 0.59 |

The sintering preceded crystallization in all the glasses (Table 2) as is evident from a comparison between DTA and HSM thermographs presented in FIG. 3, thus resulting in well sintered dense glass powder compacts after sintering in temperature range of 800-850° C. for 1 h. The crystalline content in the sintered glass powder compacts varied between 0-30 wt. % with diopside ($CaMgSi_2O_6$) as the major crystalline phase while fluorapatite may be/may not be present as a secondary crystalline phase as described in FIG. 4 and FIG. 5. The three-point flexural strength of sintered glass-powder compacts vary between 80-150 MPa while their CTE (200-600° C.) varies between $11-12 \times 10^{-6}$ $K^{-1}$.

The sintered glass powder compacts depicted the formation of HCA surface layer within 3 days of immersion in SBF solution. These results demonstrate that the bioglass compositions reported in Table 2 may be used for applications as coatings on implants as well as scaffolds for applications in orthopaedics, dentistry and tissue engineering, as detailed in the description of the invention.

EXAMPLE 4

$B_2O_3$ & $Na_2O$ Containing Glasses

The glasses with the compositions presented in the Table 3 were prepared through melt-quenching technique and crushed to powder form with mean particle sizes between 5-20 μm in accordance with the details explained in Examples 1 to 3. The amorphous nature from the glass was confirmed by analysis of DRX.

TABLE 3

Bioglass compositions (mol. %)

| Vidro | MgO | CaO | $P_2O_5$ | $SiO_2$ | $B_2O_3$ | $Na_2O$ | $CaF_2$ |
|---|---|---|---|---|---|---|---|
| BN | 13.27 | 30.97 | 2.65 | 39.82 | 4.43 | 4.43 | 4.43 |
| N | 12.99 | 30.30 | 2.60 | 45.45 | — | 4.43 | 4.43 |

Through several complementary techniques of analysis (Raman Spectroscopy, DRX, FT-IR), both glasses showed evidences of the deposition of HCA layer at the surface of the particles after 24 h of immersion in solution of SBF, the intensities of the characteristic peaks gradually increased with the time of immersion.

EXAMPLE 5

Bioglasses with Bactericidal Activity Prepared by Sol-Gel

TABLE 4

Bioglass compositions (mol. %)

| Vidro | CaO | $P_2O_5$ | $SiO_2$ | $Ag_2O$ |
|---|---|---|---|---|
| SG-BG | 26.00 | 10.00 | 64.00 | — |
| SG-AgBG | 26.00 | 5.00 | 64.00 | 5.00 |

The bioglasses SG-BG and SG-AgBG were prepared by sol-gel (SG) and were aimed at evaluating the bactericidal properties of the composition SG-AgBG contain silver oxide. All the precursors were supplied for Aldrich. The TEOS was previously hydrolysed during 1 h in a solution 0.1 M of nitric acid. To this solution there were then added successively the trietylphosphate (TEP), calcium nitrate, and silver nitrate, with an interval of 45 min between each addition as a way to promote the complete hydrolysis. The samples of SG-AgBG were handled and maintained in the darkness in order to preserve the state of oxidation +1 of the silver ion. The bio-vidro without silver, SG-BG, was prepared in a similar manner.

The solutions were sealed and maintained in a Teflon container for 10 days at the room temperature. The temperature was then increased for 70° C. and maintained for more 3 days to promote the drying, with the steam to be freed through orifices done in the lid of the container. To the end of this time, temperature was again increased for 120° C. and maintained for more 2 days for a complete drying. The dry powders were calcined for 24 h at 700° C. to stabilize the glasses and to remove the residual nitrate ions. The bacteriostatic and bactericidal capacity of both bioglasses ground up to particle sizes of 100-700 μm was tested in a liquid of culture of the *E. Coli* MG1655. The tests in vitro showed that the SG-AgBG was able to effectively kill the bacteria *E. Coli*.

EXAMPLE 6

Bioglasses with High $P_2O_5$ Contents

TABLE 5

Bioglass compositions (mol. %)

| Vidro | CaO | $P_2O_5$ | $SiO_2$ | Ca/P |
|---|---|---|---|---|
| SG-P35 | 56.00 | 35.00 | 10.00 | 1.60 |
| SG-P36 | 54.00 | 36.00 | 10.00 | 1.50 |

The bioglasses SG-P35 and SG-P36 were prepared by sol-gel (SG), The TEOS was previously hydrolysed during 1 h in a solution 0.1 M of nitric acid. The calcium nitrate, $Ca(NO_3)_2.4H_2O$, was also dissolved in this solution. A solution of diammonium phosphate, $NH_42HPO_4$, prepared in water bi-distilled water was then added jointly with nitric acid in order to adjust the pH between 3-4. The obtained sol was aged and dried following a procedure analogous to that reported in the example 5. The dried powders were then calcined at 800° C. turning in amorphous material and metal beta-tricalcium phosphate.

The results of the in vitro tests by immersing the samples in a solution of SBF showed a gradual growth and of a HAC layer along the immersion time with a similar morphology to the trabecular structure of bone.

But the compositions abridged in the present invention are not restricted to the examples given above. The Tables 6 and 7 report on a more complete series of bioglass compositions but that even so, they do not exhaust by all the means all bioglass formulations object of the present invention.

TABLE 6

FA, TCP and W bioglass composition series (mol. %)

| Glass | Formula | MgO | CaO | $P_2O_5$ | $SiO_2$ | $CaF_2$ |
|---|---|---|---|---|---|---|
| FA-0 | Di-100 | 25 | 25 | — | 50 | — |
| FA-10 | 90Di-10FA | 23.20 | 28.18 | 1.66 | 46.41 | 0.55 |

TABLE 6-continued

FA, TCP and W bioglass composition series (mol. %)

| Glass | Formula | MgO | CaO | $P_2O_5$ | $SiO_2$ | $CaF_2$ |
|---|---|---|---|---|---|---|
| FA-20 | 80Di-20FA | 21.29 | 31.57 | 3.43 | 42.57 | 1.14 |
| FA-25 | 75Di-25FA | 20.28 | 33.34 | 4.36 | 40.57 | 1.45 |
| TCP-10 | 80Di-10FA-10TCP | 21.29 | 32.00 | 3.57 | 42.57 | 0.57 |
| TCP-20 | 70Di-10FA-20TCP | 19.24 | 36.07 | 5.61 | 38.49 | 0.59 |
| TCP-30 | 60Di-10FA-30TCP | 17.06 | 40.42 | 7.79 | 34.12 | 0.61 |
| TCP-40 | 50Di-10FA-40TCP | 14.72 | 45.08 | 10.12 | 29.45 | 0.63 |
| W-10 | 70Di-20FA-10W | 18.76 | 34.11 | 3.45 | 42.52 | 1.15 |
| W-20 | 60Di-20FA-20W | 16.20 | 36.70 | 3.48 | 42.47 | 1.16 |
| W-30 | 50Di-20FA-30W | 13.60 | 39.32 | 3.50 | 42.41 | 1.17 |
| W-40 | 40Di-20FA-40W | 10.96 | 41.98 | 3.53 | 42.35 | 1.18 |
| W-50 | 30Di-20FA-50W | 8.28 | 44.68 | 3.56 | 42.30 | 1.19 |
| W-60 | 20Di-20FA-60W | 5.56 | 47.42 | 3.58 | 42.24 | 1.19 |
| W-70 | 10Di-20FA-70W | 2.80 | 50.20 | 3.61 | 42.18 | 1.20 |
| W-80 | 20FA-70W | — | 53.03 | 3.64 | 42.12 | 1.21 |

TABLE 7

TCP-20 Composition doped with Sr—, Bi— and Zn (mol. %)

| Glass | MgO | CaO | SrO | $P_2O_5$ | $SiO_2$ | $CaF_2$ |
|---|---|---|---|---|---|---|
| TCP-20 | 19.24 | 36.07 | — | 5.61 | 38.49 | 0.59 |
| Sr-2 | 19.24 | 34.07 | 2 | 5.61 | 38.49 | 0.59 |
| Sr-4 | 19.24 | 32.07 | 4 | 5.61 | 38.49 | 0.59 |
| Sr-6 | 19.24 | 30.07 | 6 | 5.61 | 38.49 | 0.59 |
| Sr-8 | 19.24 | 28.07 | 8 | 5.61 | 38.49 | 0.59 |
| Sr-10 | 19.24 | 26.07 | 10 | 5.61 | 38.49 | 0.59 |

| Glass | MgO | CaO | $Bi_2O_3$ | $P_2O_5$ | $SiO_2$ | $CaF_2$ |
|---|---|---|---|---|---|---|
| Bi-2 | 19.24 | 36.07 | 2 | 5.61 | 36.49 | 0.59 |
| Bi-4 | 19.24 | 36.07 | 4 | 5.61 | 34.49 | 0.59 |
| Bi-6 | 19.24 | 36.07 | 6 | 5.61 | 32.49 | 0.59 |
| Bi-8 | 19.24 | 36.07 | 8 | 5.61 | 30.49 | 0.59 |
| Bi-10 | 19.24 | 36.07 | 10 | 5.61 | 28.49 | 0.59 |

| Glass | MgO | CaO | ZnO | $P_2O_5$ | $SiO_2$ | $CaF_2$ |
|---|---|---|---|---|---|---|
| Zn-2 | 17.24 | 36.07 | 2 | 5.61 | 38.49 | 0.59 |
| Zn-4 | 15.24 | 36.07 | 4 | 5.61 | 38.49 | 0.59 |
| Zn-6 | 13.24 | 36.07 | 6 | 5.61 | 38.49 | 0.59 |
| Zn-8 | 11.24 | 36.07 | 8 | 5.61 | 38.49 | 0.59 |
| Zn-10 | 9.24 | 36.07 | 10 | 5.61 | 38.49 | 0.59 |

The present invention is not, naturally, in no way limited to the realizations described in this document and a person with an average background in the area will be able to predict many modification of the same without moving away of the general idea of the invention, such as defined in the claims.

The realizations above described are all interrelated in the common form.

The next claims define additionally preferential realizations of the present invention.

The invention claimed is:

1. A bioactive glass composition comprising the following components:
  (a) calcium oxide (CaO), between 20-60%;
  (b) magnesium oxide (MgO), between 14-25%;
  (c) phosphorous pentoxide ($P_2O_5$), between 0-10%;
  (d) silica ($SiO_2$) between 29-60%; and
  (e) calcium fluoride in the form of $CaF_2$, between 0-5%;
  wherein all the percentages are molar percentages, and wherein the composition is alkali-free.

2. The composition according to claim 1, wherein the phosphorous pentoxide and the silica are glass network formers.

3. The composition according to claim 1, comprising the following components:
  (a) calcium oxide (CaO), between 25-53%;
  (b) magnesium oxide (MgO), between 14-24%;
  (c) phosphorous pentoxide ($P_2O_5$), between 1.7-8%;
  (d) silica ($SiO_2$) between 29-50%; and
  (e) calcium fluoride in the form of $CaF_2$, between 0-3%;
  wherein all the percentages are molar percentages.

4. The composition according to claim 1, wherein the source of calcium is selected from at least one of the following: calcium oxide, calcium hydroxide, calcium carbonate, calcium nitrate, calcium sulphate, and calcium silicates.

5. The composition according to claim 1, wherein the source of magnesium is selected from at least one of the following: magnesium oxide, magnesium hydroxide, magnesium carbonate, magnesium nitrate, magnesium sulphate, and magnesium silicates.

6. The composition according to claim 1, wherein the source of phosphorous is selected from at least one of the following: phosphorous pentoxide, ammonium dihydrogen phosphate, trimethyl phosphafate, triethyl phosphate, phosphoric acid, and any other source of phosphorous pentoxide.

7. The composition according to claim 1, wherein the source of fluorine is selected from at least one of the following: calcium fluoride, magnesium fluoride, trifluoroacetic acid, hexafluorophosphate acid, and ammonium hexafluorophosphate.

8. The composition according to claim 1, further comprising as a doping agent at least one of the following elements: Ru, Sr, Bi, Zn, Ag, B, Cu, Mn, Fe, and Ti or an oxide thereof in a molar percentage between 0-10%.

9. The composition according to claim 1, wherein the individual molar percentage of the doping oxide varies between 0-5%.

10. The composition according to claim 1, comprising the following:
  (a) an oxide selected from the group consisting of $SiO_2$, CaO, MgO, $P_2O_5$, $Ru_2O$, SrO, $Bi_2O_3$, ZnO, $Ag_2O$, $B_2O_3$, $Cu_2O$, $MnO_2$, $Fe_2O_3$, and $TiO_2$;
  (b) an alkoxide selected from the group consisting of traethyl orthosilicate $Si(OC_2H_5)_4$ (TEOS), tetramethyl orthosilicate $Si(OCH_3)_4$ (TMOS), and titanium isopropoxide $C_{12}H_{28}O_4Ti$;
  (c) a hydroxide selected from the group consisting of $Ca(OH)_2$, $Mg(OH)_2$, and $Fe(OH)_3$;
  (d) a carbonate selected from the group consisting of $CaCO_3$, $MgCO_3$, and $SrCO_3$;
  (e) a nitrate selected from the group consisting of $Ag(NO_3)$, $Mg(NO_3)_2$, $Ca(NO_3)_2$, $Ca(NO_3)_2.4H_2O$, $Ag_2(NO_3)_2$, $Fe(NO_3)_3$, and $Fe(NO_3)_3.9H_2O$;
  (f) a sulphate;
  (g) a phosphate or phosphorus precursor selected from the group consisting of ammonium dihydrogen phosphate ($NH_4H_2PO_4$), trimethyl phosphate $(CH_3O)_3PO$ (TMP), triethyl phosphate $(C_2H_5O)_3PO$ (TEP), and phosphoric acid;
  (h) a fluoride or fluorine precursor selected from the group consisting of calcium fluoride $CaF_2$, magnesium fluoride ($MgF_2$), trifluoroacetic acid $CF_3COOH$ (TFA), hexafluorophosphoric acid ($HPF_6$), and ammonium hexafluorophosphate ($NH_4PF_6$) or a chloride selected from the group consisting of $CaCl_2$, $MgCl_2$, and $FeCl_3$; and
  (i) a borate.

11. The composition according to claim 1, further comprising a polymeric resin.

12. The composition according to claim 1, in powder form.

13. The composition according to claim 1, in the form of particles with sizes less than 500 mm.

14. The composition according to claim 1, further comprising injectable cements based on calcium phosphates or on polymethylmethacrylate.

15. The composition according to claim 1, in the form of a prosthesis, implant, tooth paste, dental cement, or bone filler.

16. The composition according to claim 1, for use in the synthesis in vitro of bone tissue.

17. The composition according to claim 15, in the form of a coating on an implant.

18. The composition according to claim 17, wherein the prostheses is made of a chromium cobalt alloy, stainless steel, a titanium alloy, a polymeric material, a ceramic material or mixture of two or more of the foregoing.

* * * * *